(12) United States Patent
Sanders

(10) Patent No.: US 7,074,757 B2
(45) Date of Patent: Jul. 11, 2006

(54) METHOD AND DEVICE FOR IMPROVING PROTEIN STABILITY AND SOLUBILITY

(75) Inventor: Mitchell C. Sanders, West Boylston, MA (US)

(73) Assignee: Expressive Constructs, Inc., Worcester, MA (US)

( * ) Notice: Subject to any disclaimer, the term of this patent is extended or adjusted under 35 U.S.C. 154(b) by 0 days.

(21) Appl. No.: 11/070,388

(22) Filed: Mar. 1, 2005

(65) Prior Publication Data

US 2005/0272864 A1 Dec. 8, 2005

Related U.S. Application Data

(63) Continuation of application No. 09/848,780, filed on May 3, 2001, now Pat. No. 6,861,403.

(60) Provisional application No. 60/201,407, filed on May 3, 2000.

(51) Int. Cl.
*C07K 1/14* (2006.01)
*C07K 1/10* (2006.01)

(52) U.S. Cl. .......................... 514/2; 530/412; 530/350; 530/378.3; 435/440; 514/12

(58) Field of Classification Search .................... 514/2, 514/12; 530/378.3, 412, 350; 435/440
See application file for complete search history.

(56) References Cited

U.S. PATENT DOCUMENTS

| | | |
|---|---|---|
| 5,804,417 A | 9/1998 | Martens et al. |
| 5,989,868 A | 11/1999 | Harrison et al. |
| 6,207,420 B1 | 3/2001 | Harrison et al. |
| 6,310,186 B1 | 10/2001 | Wilson et al. |
| 6,455,279 B1 | 9/2002 | Ambrosius et al. |
| 6,861,403 B1 * | 3/2005 | Sanders .................. 514/2 |
| 2002/0177192 A1 | 11/2002 | Siva et al. |

FOREIGN PATENT DOCUMENTS

| | | |
|---|---|---|
| JP | 09 299092 | 11/1997 |
| WO | WO 93/13200 | 7/1993 |
| WO | WO 95/33997 A1 | 12/1995 |
| WO | WO 01/83804 A1 | 11/2001 |
| WO | WO 02/48190 A1 | 6/2002 |
| WO | WO 03/063693 A2 | 8/2003 |
| WO | WO 03/102227 A1 | 12/2003 |

OTHER PUBLICATIONS

Ueda et al. (2002) Mass measurements of C-terminally truncated alpha-crystallins from two-dimensional gels identify Lp82 as a major endopeptidase in rat lens. Mol. Cell. Proteomics. vol. 1, No. 15, pp. 357-365.*
Usha et al. (2002) The R116C mutation in alpha A-crystallin diminishes its protective ability against stress-induced lens epithelial cell apoptosis. J. Biol. Chem. vol. 277, No. 12, pp. 10178-10186.*
Davis, G.D. et al., "New Fusion Protein Systems Designed to Give Soluble Expression in *Escherichia coli*," *Biotech. and Bioeng.*, 65(4): 382-388 (1999).
Goodwin, E.C.and Rottman, F.M., "The 3'-Flanking Sequence of the Bovine Growth Hormone Gene Contains Novel Elements Required for Efficient and Accurate Polyadenylation," *J. Biol. Chem.*, 267(23):16330-16334(1992).
Harrison, R.G., "Expression of Soluble Heterologous Proteins via Fusion with NusA Protein," *Innovations*, 11:4-7 (2000).
Kim, K.K. et al., "Crystal Structure of a Small Heat-shock Protein," *Nature*, 394:595-599 (1998).
Koo, J. et al. "Antacid Increases Survival of *Vibrio vulnificus* and *Vibrio vulnificus* Phage in a Gastrointestinal Model," *Applied and Environmental Microbiology*, 67(7):2895-2902 (2001).
Liang P. and MacRae, T.H.,"The Synthesis of Small Heat Shock/α-crystallin Protein in *Artemia* and its Relationship to Stress Tolerance During Development," *Dev. Biol.*, 207(2):445-456 (1999).

(Continued)

*Primary Examiner*—Jon Weber
*Assistant Examiner*—Samuel Wei Liu
(74) *Attorney, Agent, or Firm*—Hamilton, Brook, Smith & Reynolds, P.C.

(57) ABSTRACT

A method for expressing proteins as a fusion chimera with a domain of p26 or alpha crystallin type proteins to improve the protein stability and solubility when over expressed in bacteria such as *E. coli* is provided. Genes of interest are cloned into the multiple cloning site of the Vector System just downstream of the p26 or alpha crystallin type protein and a thrombin cleavage site. Protein expression is driven by a strong bacterial promoter (TAC). The expression is induced by the addition of 1 mM IPTG that overcomes the lac repression (lac $I_q$). The soluble recombinant protein is purified using a fusion tag.

5 Claims, 5 Drawing Sheets

OTHER PUBLICATIONS

MacRae, T.H., "Structure and Function of Small Heat Shock/α-crystallin Proteins: Established Concepts and Emerging Ideas," *Cell Mol. Life Sci.*, 57(6):899-913 (2000).

Marini I. et al., "Alpha-Crystallin-Like Molecular Chaperone Against the Thermal Denaturation of Lens Aldose Reductase: The Effect of Divalent Metal Ions," *Biochemical and Biophysical Research Communications*, 212(2):413-420 (1995).

Sun T-X. et al., "Conformational and Functional Differences between Recombinant Human Lens αA- and αB-Crystallin," *J. Biol. Chem.*, 272(10):6220-6225 (1997).

Wilkinson, D.L. and Harrison, R.G.,"Predicting the Solubility of Recombinant Proteins in *Eschericia coli*," *Bio/Technology*, 9:443-448 (1991).

Liang, P. et al., "Purification, structure and *in vitro* molecular-chaperone activity of *Artemia* p26, a small heat-shock/α-crystallin protein," *European Journal of Biochemistry*, 243(1-2):225-232 (1997).

Ortwerth, B.J. et al., "Chemical Modification of Alpha Crystallin," *Exp. Eye Res.*, 56(1):107-114 (1993).

Sachdev, D. et al., "Order of Fusions between Bacterial and Mammalian Proteins Can Determine Solubility in *Escherichia coli*," *Biochemical and Biophysical Research Communications*, 244(3):933-937(1998).

Hayhurst, A., "Improved Expression Characteristics of Single-Chain Fv Fragments When Fused Downstream of the *Escherichia coli* Maltose-Binding Protein or Upstream of a Single Immunoglobulin-Constant Domain," *Protein Expression and Purification*, 18(1):1-10 (2000).

Luo, Z-H. et al., "Increased Solubility of Glutathione S-Transferase-P16 (GST-P16) Fusion Protein by Co-Expression of Chaperones Groes and Groel in *Escherichia coli*," *Biochemistry and Molecular Biology International*, 46(3):471-477 (1998).

Kapust, R.B. et al., "*Escherichia coli* Maltose-Binding Protein is Uncommonly Effective at Promoting the Solubility of Polypeptides to which it is Fused," *Protein Science*, 8(8):1668-1674(1999).

Andley, Usha P. et al., "Cloning, Expression, and Chaperone-like Activity of Human αA-Crystallin," *J. Biol. Chemistry*, 271(50): 31973-31980 (1996).

Pilon, A.L. et al., "High-level Expression and Efficient Recovery of Ubiquitin Fusion Proteins from *Escherichia coli*," *Biotechnol Prog.* 12:331-337 (1996).

Wittliff, J.L. et al., "Expression and Characterization of an Active Human Estrogen Receptor as a Ubiquitin Fusion Protein from *Escherichia coli*," *J. Biol Chem.*, 265:22016-22022 (1990).

Wagner, B. L. et al., "Age-dependent Association of Isolated Bovine Lens Multicatalytic Proteinase Complex (Proteasome) with Heat-shock Protein 90, and Endogenous Inhibitor," *Arch Biochem Biophys. 323*:455-462 (1995).

Adams, J. et al., "Proteasome Inhibitors: A Novel Class of Potent and Effective Antitumor Agents," *Cancer Res.*, 59:2615-2622 (1999).

Gopalakrishnan, S. et al., "An Assay for Intermolecular Exchange of Alpha Crystallin," *Invest Ophthalmol Vis Sci.*, 33:2936-2941 (1992).

Reddy, G. B. et al., "Temperature-dependent Chaperone Activity and Structural Properties of Human AlphaA- and AlphaB- Crystallins," *J. Biol. Chem.*, 275:4565-4570 (2000).

Cobb, A. et al., "Characterization of α-Crystallin-Plasma Membrane Binding," *J. Biol. Chem.*, 275(9):6664-6672 (2000).

Guo, Z. et al., "An N-terminal 33-amino-acid-deletion Variant of hsp25 Retains Oligomerization and Functional Properties," *Biochem Biophys Res Commun.*, 270:183-189 (2000).

Stevens, A. et al., "Isolation of Alpha-crystallin Subunits by Gel Filtration," *Curr. Eye Res.*, 6:739-740 (1987).

* cited by examiner

SEQUENCE LISTING

```
<160> NUMBER OF SEQ ID NOS: 1

<210> SEQ ID NO 1
<211> LENGTH: 41
<212> TYPE: DNA
<213> ORGANISM: Artificial Sequence
<220> FEATURE:
<223> OTHER INFORMATION: Designed oligonucleotide sequence to act as a
      multiple cloning site in a vector.
```

-continued

```
<400> SEQUENCE: 1
catatggctg cagatcgccc gggctcgagg agctcgaatt c                    41
```

METHOD AND DEVICE FOR IMPROVING PROTEIN STABILITY AND SOLUBILITY

RELATED APPLICATIONS

This application is a continuation of U.S. application Ser. No. 09/848,780, filed May 3, 2001, now U.S. Pat. No. 6,861,403, issued Mar. 1, 2005, which claims the benefit of U.S. Provisional Application No. 60/201,407, filed May 3, 2000. The entire teachings of the above applications are incorporated herein by reference.

GOVERNMENT SUPPORT

The invention was supported, in whole or in part, by a grant GM59535-01 from the National Institutes of Health. The government has certain rights in the invention.

FIELD OF INVENTION

This present invention relates to a method and a device for improving protein folding, solubility, and stability when the protein is produced in vivo and in vitro.

BACKGROUND OF INVENTION

High throughput screening (HTS) of protein targets for drug discovery is a very costly process. On average it cost about $100 million dollars to develop one drug and only three percent of the drugs make it through phase I clinical trials. About 5–15% of all proteins targets that are chosen for HTS never make it into the pipeline because the proteins are either insoluble, inactive, or unstable (sensitive to proteolysis). Although yeast and baculovirus systems for gene expression are often used as reliable alternatives, bacterial expression systems are still the main method of choice for over expressing recombinant proteins for drug development studies.

Protein insolubility is one of the major problems associated with over-expressing proteins in bacteria. Protein solubility is judged empirically by assaying the levels of recombinant protein in the supernatant and pellet of lysed protein extracts. In general, small proteins (>30 kD) that are simple monomeric proteins can be found in the soluble fractions of bacterial extracts. In contrasts, proteins (<30 kD) or proteins that have complex secondary or tertiary structures are typically insoluble and are predominantly found in inclusion bodies. Although insoluble proteins can be denatured in urea and refolded in situ, full activity frequently is not restored.

Yet another problem associated with the recombinant expression of proteins is proteolysis in vivo. Although a number of proteases have been removed by gene knock out technologies to reduce proteolysis in bacterial expression systems (such as lon in BL21 DE3), many proteins are very sensitive to endogenous bacterial proteases. Sensitivity to proteases can dramatically reduce the yield of full-length recombinant proteins. In extreme cases the expression of recombinant proteins is nearly undetectable due to proteolysis.

OBJECT OF THE INVENTION

It is an object of the present invention to provide a method for expressing insoluble proteins It is an object of the present invention to provide a method for expressing proteins that are sensitive to proteolysis.

It is an object of the present invention to provide a method for removing protease from protein extracts.

It is an object of the present invention to provide a method for using p26, SicA, and alpha crystallin type proteins in biochemical assays to remove non-specific protein interactions.

SUMMARY

The present invention provides a method and a device for improving target protein folding, solubility, and stability when the target protein is produced in vivo and in vitro. In one embodiment, the present invention provides a method for expressing target proteins in a plasmid system as a fusion (chimera) having a domain of p26, SicA, or alpha crystallin type proteins to improve the target protein stability and solubility when the target protein is over expressed in bacteria such as E. coli. The method comprises inserting a gene coding for a target protein into a multiple cloning site (MCS) of a vector system, proximal to and just downstream of the p26, SicA or alpha crystallin type protein coding site or domain that is adjacent to a thrombin cleavage site and then expressing the target protein. Preferably, the target protein when expressed in the absence of the inventive vector construct is insoluble and accumulates in inclusion bodies in the cells. Target protein expression in the inventive vector system is driven for example by a strong bacterial promoter such as (TAC). Other strong promoters would give comparable results. The expression is induced for example by the addition of 1 mM Isopropyl β-D-Thiogalactopyranoside (IPTG) that de-represses the lac repressor protein (lac I$^q$). The method includes purifying the target protein produced by the expression system. In one embodiment, the soluble recombinant target protein is purified for example using a fusion tag (polyhistidine; Hoffman La Roche; Basel, Switzerland) Further, the p26, SicA, or alpha-crystallin type protein domain can be removed by thrombin cleavage.

In another aspect of the present invention, a device that acts as a pre-column filter for reducing unwanted proteolysis on a chromatography column during purification of a target protein is provided. The pre-column filter is an affinity chromatography resin useful for removing proteases from crude protein extracts. In one embodiment, the pre-column filter comprises bovine lens alpha crystallin coupled to cyanogen bromide activated sepharose (CNBr-sepharose).

The vector comprises the active anti-parallel beta sheets and the active charged core domain of p26, a small molecular chaperone/α-crystallin type protein from the brine shrimp Artemia. When this active domain of p26 is fused to a gene target, the recombinant expression of that gene target produces soluble recombinant target proteins. As used herein "charged core domain" is defined as the amino acid residues 160–192. As used herein the active anti-parallel beta sheets is defined by amino acid residues 36–160. As used herein the term "otherwise insoluble protein" is defined as a protein that is insoluble when expressed in a prior art vector system such as the pET28a over-expression vector; trademarked Kan (Novagen, Inc., Carlsbad, Calif.). Examples of otherwise insoluble proteins expressed in E. coli include pepsinogen, and procathepsin D.

As used herein, the term "fusion tag" or "protein fusion" is defined as a DNA molecule that is added to a gene that is expressed in frame thereby making a protein chimera. Examples of suitable fusion tags include but are not meant to be limited to: polyhistidine; glutathione; maltose binding protein; S protein; and beta-galactosidase.

The target gene for the otherwise insoluble protein is inserted in frame into the poly-linker region of the vector plasmid just downstream of the beta-core domain of p26 (Vector S) or the entire alpha-A-crystallin (Vector AP) A thrombin cleavage site provides for a removable fusion tag.

| | |
|---|---|
| VECTOR-S (S = soluble) | Fusion domain p26 or SicA |
| VECTOR-AP (AP = anti-proteolysis) | Fusion domain of α-A crystallin |

Unexpectedly, alpha-A-crystallin, but not p26 or SicA is shown to result in a reduction in unwanted proteolysis.

DETAILED DESCRIPTION OF THE INVENTION

Figure 1:
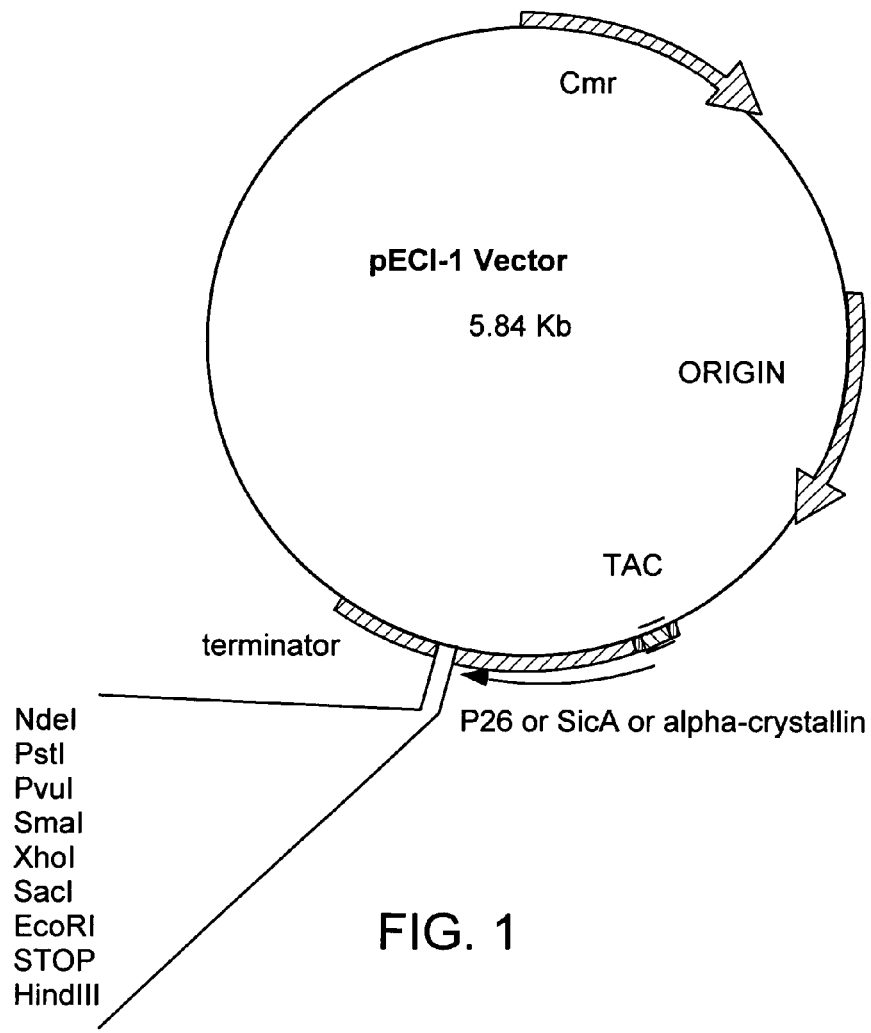
FIG. 1. shows a plasmid map for the Vector System DNA construct.

Referring to FIG. 1, an expression vector consisting of a gene fusion between an unstable or insoluble protein could be stabilized or protected from proteolysis with the appropriate class of small molecular chaperone/alpha crystallin type proteins such as p26 from *Artemia*, SicA from Salmonella and alpha-A-crystallin protein from bovine lens. Unexpectedly it was shown that the protein p26 from *Artemia* has an active domain that can assist in the formation of soluble proteins based on its properties as an alpha-crystallin type protein. It was determined that full-length p26 protein is completely insoluble when express in *E. coli* at 37° C. It is expected that proteins with a similar structural fold such as the SicA protein from *Salmonella typhimurium* could be substituted for p26. These results indicate that p26 and SicA are functionally very similar. It is also envisioned that the chaperone could be co-expressed on two different promoters either on the same plasmid or on different plasmids in the bacteria. The advantages of co-expression are that it would not require the removal of a fusion tag (such as thrombin) prior to purifying the protein of interest.

Here it is demonstrated that not all alpha-crystallin type proteins are identical. In particular, bovine lens alpha-A-crystallin but not the p26 protein from *Artemia* or the SicA protein from *Salmonella typhimurium* was shown to specifically inhibit proteases. By expressing alpha-A-crystallin in *E. coli* it would be possible to stabilize normally unstable recombinant proteins. By providing a means to protect recombinant proteins from unfavorable proteolysis in vivo, it would be possible to develop many targets that were previous dropped from high throughput screening (HTS) programs.

Figure 2:
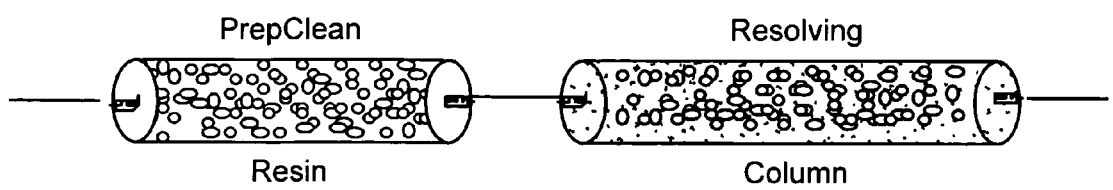
FIG. 2. is a representation of a pre-column filter placed in series with a resolving column such as a gel filtration or an ion exchange column.

Referring now to FIG. 2, One mg of bovine lens alpha crystallin is coupled per ml of CNBr—Sepharose (Lot# 276930, cat # 17-0430-01, Amersham Pharmacia Biotech) at 4° C. for overnight. Following blocking for 1 hr with 100 mM Tris, the resin is introduced into a column. If the resolving column is gel filtration, the pre-column filter remains in series throughout the entire run. For ion exchange, the pre-column filter is removed just after loading the protein sample on the column. The pre-column filter removes unwanted proteases thereby improving the purity and yield of purified proteins. Optimal conditions for the buffer are pH 7–8 and low ionic strength (<100 mM salt, NaCl or KCl).

When lens alpha-A-crystallin was coupled to chromatography resins, it was determined that it was effective in killing 85% of elastase. One ml of alpha-A-crystallin protein (at 1 mg/ml) was coupled to 100 µl swollen cyanogen bromide activated (CNBr) sepharose 4B resin according to Amersham Pharmacia (Piscataway, N.J.). Briefly, CNBr powder was swollen in 1 mM HCl, then washed with 1 mM HCl. Purified alpha-A-crystallin was dialyzed overnight into coupling buffer (0.1 M $NaHCO_3$ pH 8.3, 500 mM NaCl), with 50% glycerol. One ml of protein was added per 100 µl resin and coupled overnight at 4° C. with shaking. Five volumes of coupling buffer was used to rinse away excess protein, and the resin was then blocked with 0.1 M Tris pH 8.0 for 2 hrs at room temp. The resin was then ready for use. Other types of resins that may also work include N-hydroxysuccinimide-activated (NHS) sepharose, aldehyde-agarose, 6-aminohexanoic acid matrices, and epoxy-activated matrices. Our findings indicate that a brief acid wash (pH 2.5) would remove the bound proteases thereby rejuvenating the resin.

Bovine α-crystallin and P26 from the brine shrimp *Artemia* have strong sequence identity and represent similar structural domains or folds (secondary structure). In particular, the most striking feature is the ~10 pleated beta sheets that are responsible for the oligomerization of this class of proteins. The oligomerization of alpha crystallin type proteins is thought to be necessary for the molecular chaperone activity. Unexpectedly, it was discovered that the first five anti-parallel beta sheets of p26 (amino acid residues 35–95) are sufficient for molecular chaperone activity. However, addition of the charged c-terminal core of p26 to the vector system improves the effectiveness of the chaperone activity probably by stabilizing the oligomerization process or improving the solubility of the oligomers. SicA was cloned from *Salmonella typhimurium* and the gene was inserted into an expression vector. The α-A-crystallin gene was cloned from neonate bovine lens and inserted into an expression vector. Two clones of the entire p26 gene were used (p26pRSET C, p26pET21 from Tom MacRae of Dalhousie University (Halifax, Nova Scotia)). In addition to these full-length constructs, the entire p26 gene and three smaller domains were amplified by polymerase chain reaction for fusion expression studies. The entire p26 gene was cloned into the inventive expression vector. The inventive vector system contains the p15a origin of replication for co-expression studies. However, other origins can be used such as, for example, a ColE1 origin derived from pBR322. The p26 fusion domains were designed with an Nde 1 site at the carboxy terminus of p26 so that insoluble target proteins can easily be placed downstream. The vector construction is described in more detail in the next paragraph. Pepsinogen was used as a test target protein for the co-expression studies because it was shown to be completely insoluble when expressed in *E. Coli* (Sachdev et al. 1998).

Vector Construction

The initial step in the vector construction was to replace the MCS found in the PKK223-3 vector with a newly constructed MCS. The new MCS knocked out the EcoRI site at base position 4584 and placed it further downstream in the new MCS (see FIG. 1). The first restriction site found in the new MCS is an NdeI site which will be used for future in frame cloning. The vector contains pACYC184 as the vector backbone. A portion of the tetracycline gene in pACYC184 was deleted (BamHI to NruI) and replaced with the tac promoter, a newly constructed MCS, and the rrnb ribosomal terminator (from the pKK223-3 vector, BamHI to ScaI). The inventive MCS had the following sequence:

CATATGGCTGCAGATCGCCCGGGCTCGAGGAGCTCGAATTC (SEQ. 1)

The p26 betacore domain was amplified using a forward primer containing an AseI site and a reverse primer containing the thrombin cleavage site as well as an NdeI site. The p26 betacore cloning strategy was designed to knockout the NdeI site upstream of the betacore domain and place it downstream of the thrombin cleavage site. Allowing for future cloning of insoluble proteins downstream of the p26 betacore domain. The lac I$^q$ gene was cloned into the AhdI-DrdI site of the vector. The lacI$^q$ gene was PCR amplified from the *E. coli* strain MG1655. The forward primer contained an AhdI site and the reverse primer contained a DrdI site. The final vector size after all inserts were made is ~5.85 Kb.

Materials Used in Vector Construction

MG 1655 kind gift from Terri Kenney of Genome Therapeutics (Waltham, Mass.)

P26 pRSETC kind gift from Tom MacRae

PKK223-3 Vector Amersham Pharmacia cat.# 27-4935-01 lot# 8054935011 pACYC184 NEB cat.# 401M Bio-Rad quantum prep plasmid midiprep kit cat.# 732-6120

Qiagens qiafilter plasmid midiprep kit cat.#12243 lot#AMG006/BQ1069/GO1/128

Oligonucleotides for MCS Oligo1: BRL# M4469B07 Oligo2: BRL# M4469B08

Oligonucleotides for p26 betacore amplifications NdeKO-For2, BRL# M9153B05

Thrombin Rev. BRL# M8902D08

Oligonucleotides for α-A-crystallin amplifications alpha-a BRL#10336-022 alpha-a rev BRL# N2571D10.

Oligonucleotides for SicA amplification SicAFor BRL# N5263G12 and SicA Rev: BRL# N5263h01.

Primers for lacI$^q$: lacI for. BRL#N2757F05 lacI rev2 BRL#N3305D03

Qiagen Qiaquick PCR Purification Kit cat.# 28104 Lot#BYG015/G01/178

Qiagen Qiaprep Spin Miniprep Kit cat.#27104 lot# BXG038/GO3/318

Taq DNA Polymerase BRL cat.#10342-020 lot#1059060

Figure 3:
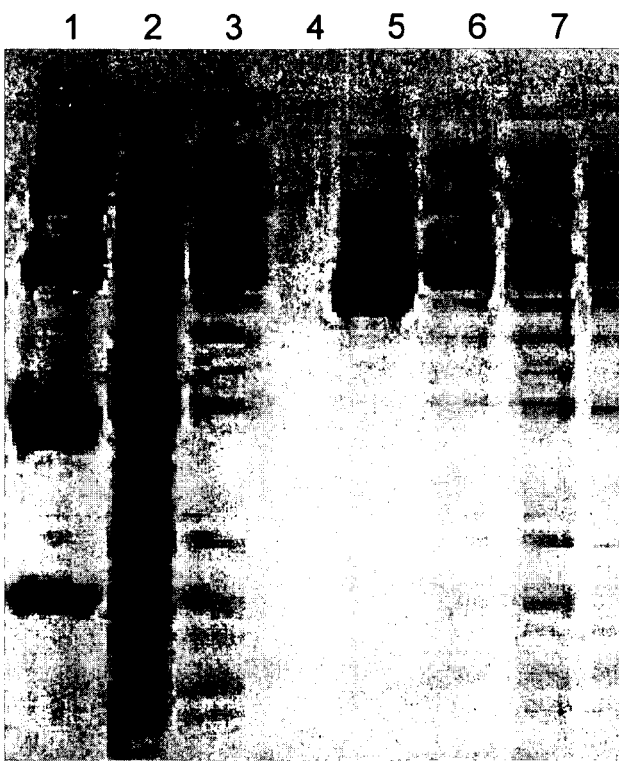
FIG. 3 is a digital image of a sodium dodecyl sulfate polyacrylamide gel electrophoresis (SDS PAGE gel) showing purified BC-pepsinogen.

Referring to FIG. 3 a IL culture of BL21(DE3) cells containing betacore-pepsinogen was induced with 1 mM IPTG for 4 hours. The cells were centrifuged and lysed by sonication. The lysate was clarified by centrifugation, 0.2 μm filtered, and loaded onto the 1.6 ml affinity column. The BC-pepsinogen protein was eluted with a linear gradient of NaCl (0–1 M). The lane order was: 1 protein standard, 2, column load, 3, flow through, 4-7 fractions from NaCl gradient. Fraction 5 contained the purified BC-pepsinogen chimeric protein. Fusion of target genes coding for insoluble proteins to the beta pleated sheet and charged core domain of p26 improves the solubility of these proteins (FIG. 3). It is envisioned that the inventive vector system will be very useful for improving the solubility of normally insoluble proteins such as for example immunoglobulin domains, proteases, cytokines, release factors and insoluble antigens.

Method for the Purification of p26

Figure 4:
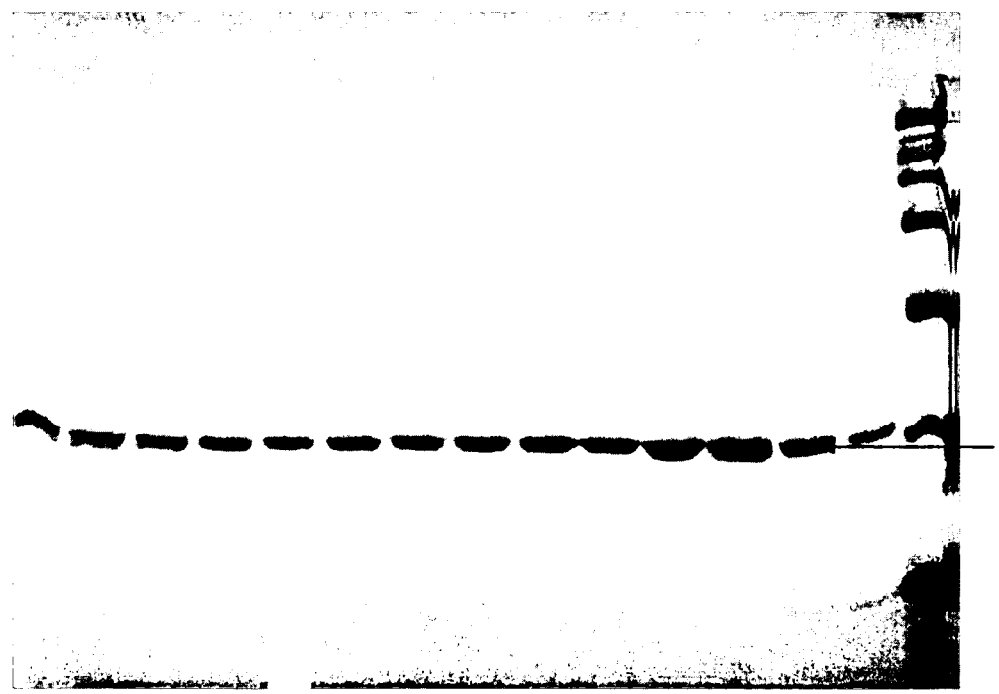
FIG. 4 shows a digital image of a 12% SDS PAGE gel of p26 protein purified by nickel affinity chromatography resin. Because p26 is a multi-oligomer, it has a tendency to elute over several fractions, even when a sharp gradient is provided. Fractions identified using the SDS gel and containing p26 are dialyzed into Pipes magnesium buffer (20 mM piperazine- 1,4-bis(2-ethanesulphonic acid (Pipes) pH 7.0, 1 mM $MgCl_2$). Following dialysis the target protein was stored at −20 C. and used in less than 1 week for kinetic assays and chromatography experiments.

The entire p26 protein was expressed by growing *E. coli* to an optical density of about 1.0 and then inducing 4 hours with 1 mM IPTG. P26 protein was purified with $Ni^{2+}$-NTA sepharose (Qiagen, cat #30410,) using the detergent DECAMEG (Calbiochem, cat#373272, lot#b27260) to gently strip the protein contaminants that are nonspecifically bound to the p26 in the crude extract. At 37° C., all of the protein is in inclusion bodies, thus, an inclusion body prep was used to purify the protein. Briefly, following lysis by 3×15 sec bursts of sonication, the cell extract is centrifuged at 13 k revolutions per minute (RPM) for 15 minutes. The pellet was resuspended in low buffer (10 mM Tris pH 8.0, 500 mM NaCl) with 0.1% detergent (HECAMEG) with protease inhibitors (1.5 μg/ml leupeptin, 1.0 μM pepstatin, 0.2 μM phenylmethanesulfonyl fluoride (PMSF)). The insoluble protein was recentrifuged and the pellet was resuspended in low buffer with 1% detergent. After centrifuging the sample one time, the pellet was resuspended in 8M Urea. Low ionic strength buffer is used to bring the solution to 4 M urea, the sample was centrifuged again, and the supernatant was filtered through a 0.2 μm filter and loaded onto a nickel sepharose column. After loading the column, the p 26 was refolded with a linear reverse gradient of Urea (4–0 M Urea in low buffer). The protein bound to the column is washed with a 0.1% detergent to remove protein contaminants and the p26 is eluted with a linear gradient of high Imidazole buffer (10 mM Tris, 50 mM NaCl, 250 mM Imidazole). The protein fractions were run on a 12% SDS PAGE gel to determine which fractions were to be pooled. FIG. 4 shows a digital image of a 12% SDS PAGE gel of p26 protein purified by nickel affinity chromatography resin. Because p26 is a multi-oligomer, it has a tendency to elute overt several fractions, even when a sharp gradient is provided. Fractions identified to contain protein using the SDS gel were dialyzed into Pipes-magnesium buffer (10 mM Pipes, PH 7.0, 1 mM $MgCl_2$, 50% glycerol). The high glycerol in the dialysis buffer concentrates the protein five times and the typical yield is about 5 mg/L. Following dialysis the target protein was stored at −20° C. and used in less than 1 week for kinetic assays and chromatography experiments.

Figure 5B:
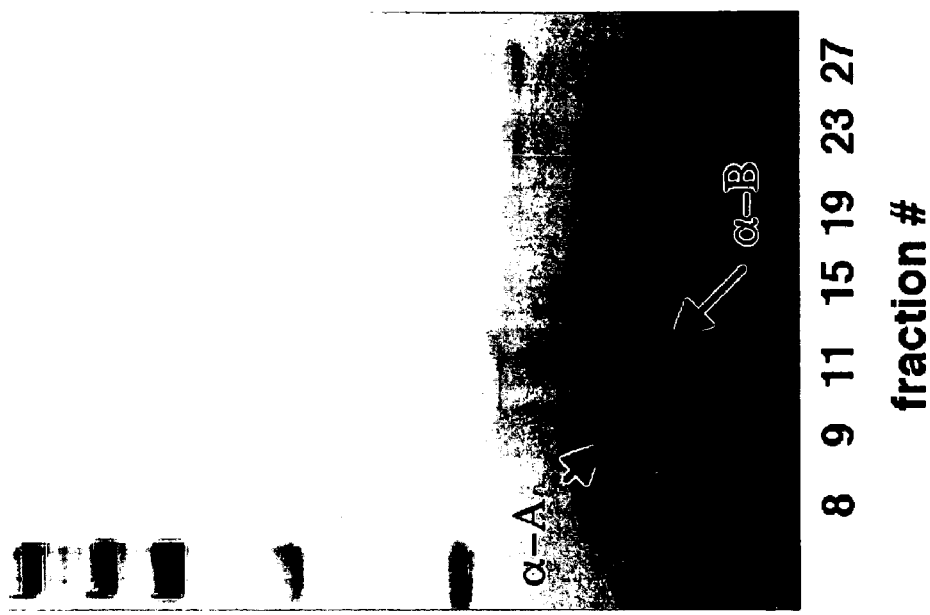
FIG. 5B provides a digital image of an SDS PAGE gel of purified α-cystallin. The pooled fractions comprise a hetero-oligomer of α-A and α-B crystallin. The top band indicated by the arrow is α-A crystallin whereas the lower band is α-B crystallin.
Figure 5A:
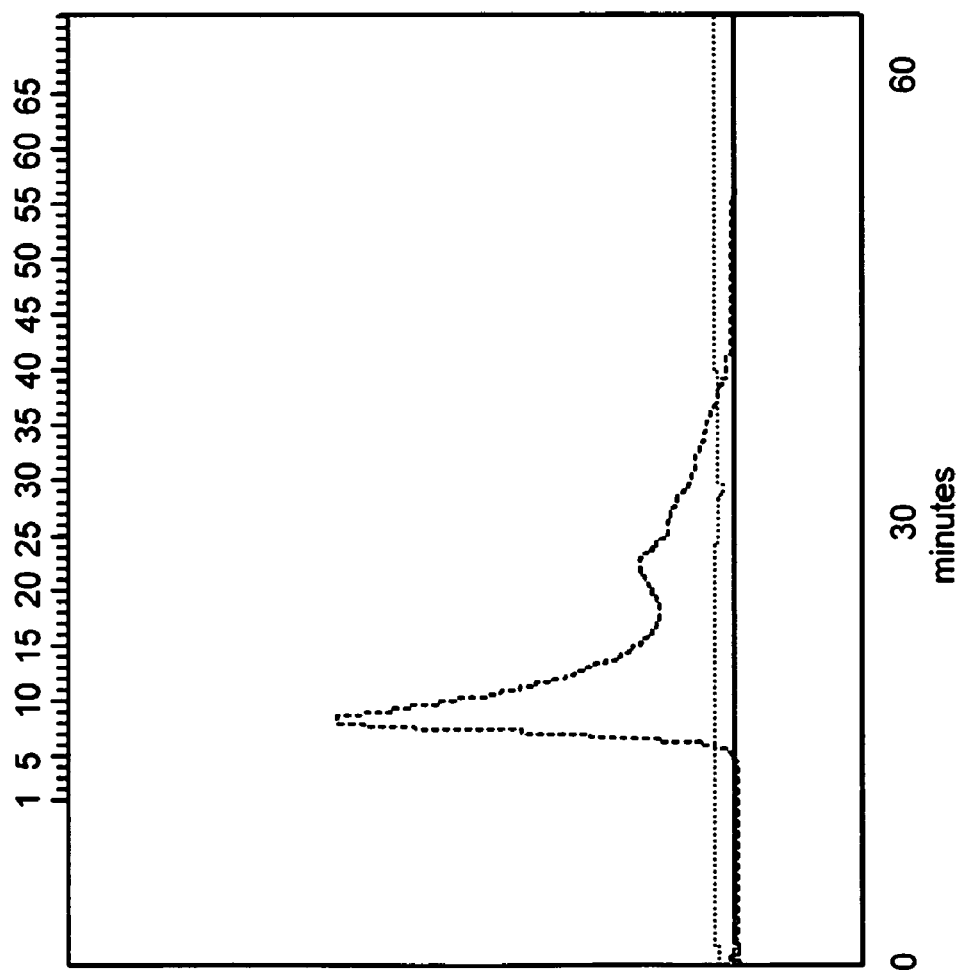
FIG. 5A shows the chromatograph of purified α-crystallin.

Method for the Purification of Alpha-Crystallin

α-crystallin was purified from bovine lens using a modification of the procedure described by Stevens (FIG. 5). Alternatively α-crystallin was expressed and purified in *E. Coli* using a procedure similar to that described for the bovine preparation above. Briefly 1 lens obtained from Animal Technologies (Tyler, Tex.) was stirred for 60 min at 4° C. with 5 ml of water and protease inhibitors (same as above). The protein was centrifuged at 13k rpm for 30 min and the supernatant was filtered through a 0.2 μm filter prior to loading on a quaternary amine sepharose 5 ml HiTrap (catalog # 17-1154-01, lot # 276218; Amersham Pharmacia Biotech; Uppsala Sweden) column. The column was rinsed until the O.D. returned to baseline and the protein was eluted with a linear gradient of NaCl (50 mM-1 M). The fractions determined to contain α-crystallin were dialyzed for 18 hours against 10 mM Tris pH 8.0, 50% glycerol. 100 μl of 1 M glycine pH 2.5 is added to 1 ml of the dialyzed solution and then run on a 10 mm×300 mm BioRad Macroprep SE 1000/40 gel filtration column. The selected fractions were quickly neutralized with 0.2 M Tris, pH 8.0 and the fractions containing the protease inhibition activity were pooled and dialyzed into 10 mM sodium bicarbonate buffer for coupling to resin (10 mM $NaHCO_3$ pH 8.0, 50% glycerol). The dialysis step is necessary because the elastase inhibition activity is strongly affected by ionic strength. The pooled fractions comprise a hetero-oligomer of α-A and α-B crystallin. Unlike the recombinant p26 which has a limited storage life the α-crystallin stored at −20° C. was very stable. FIG. 5A shows the chromatograph of purified α-crystallin. FIG. 5B provides a digital image of an SDS PAGE gel of purified α-crystallin.

Use of alpha-A-crystallin as a Protease Affinity Chromatography Resin

Figure 6:
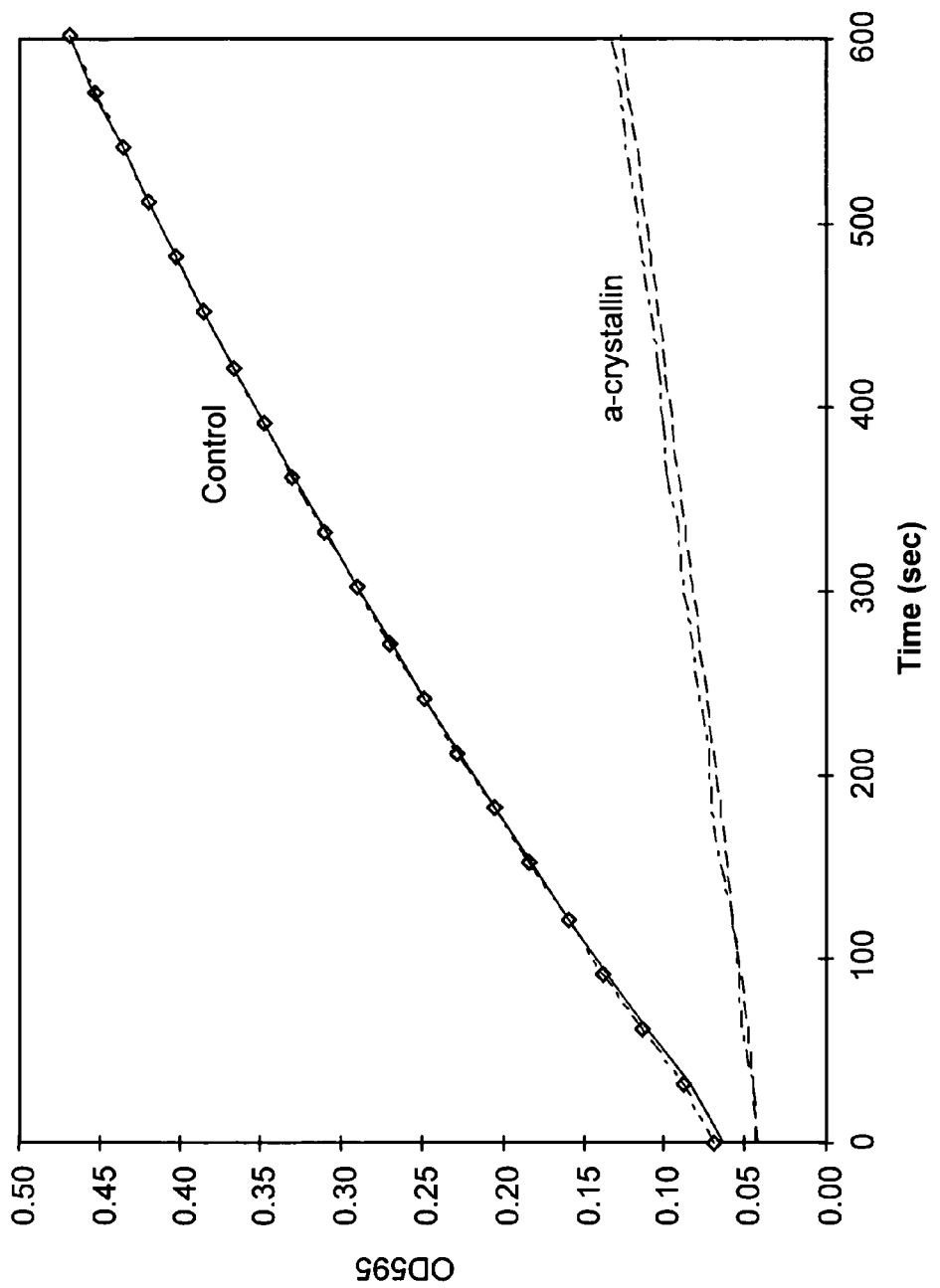
FIG. 6 provides a graph that shows the inhibition of elastase activity with α-crystallin. Elastase activity was measured using a para-nitroanaline substrate obtained from Calbiochem (La Jolla, Calif.). Assays were performed with a Benchmark microplate reader (Bio-Rad). Elastase was purchased from either Sigma or Calbiochem. In a 100 µl assay 50 µg of peptide substrate, 1 µg of elastase, and 50–100 µg of either uncoupled p26, α-crystallin conjugated sepharose, BSA conjugated sepharose, or buffer (negative control) was used.

The ability of α-crystallin or p26 coupled to CNBR Sepharose to inhibit elastase was examined by using a paranitroanilide substrate for elastase (Calbiochem, Cat# 324696, Lot #B27708). FIG. 6 provides a graph that shows the inhibition of elastase activity with α-crystallin. Elastase activity was measured using a para-nitroanaline substrate obtained from Calbiochem (La Jolla, Calif.). Assays were performed with a Benchmark microplate reader (Bio-Rad). Elastase was purchased from either Sigma or Calbiochem. In a 100 μl assay 50 μg of peptide substrate, 1 μg of elastase, and 50–100 μg of either uncoupled p26, α-crystallin conjugated sepharose, BSA conjugated sepharose, or buffer (negative control) was used.

Findings indicate that α-crystallin sepharose inhibits up to 85% of the elastase in protein extracts. The inventive pre-column filters can be regenerated with low pH solutions since α-crystallin is stable for a brief period in 0.1 M glycine pH 2.5. The lack of protease inhibition by p26 suggests that p26 and bovine lens α-crystallin are less similar than previously speculated.

Figure 7:
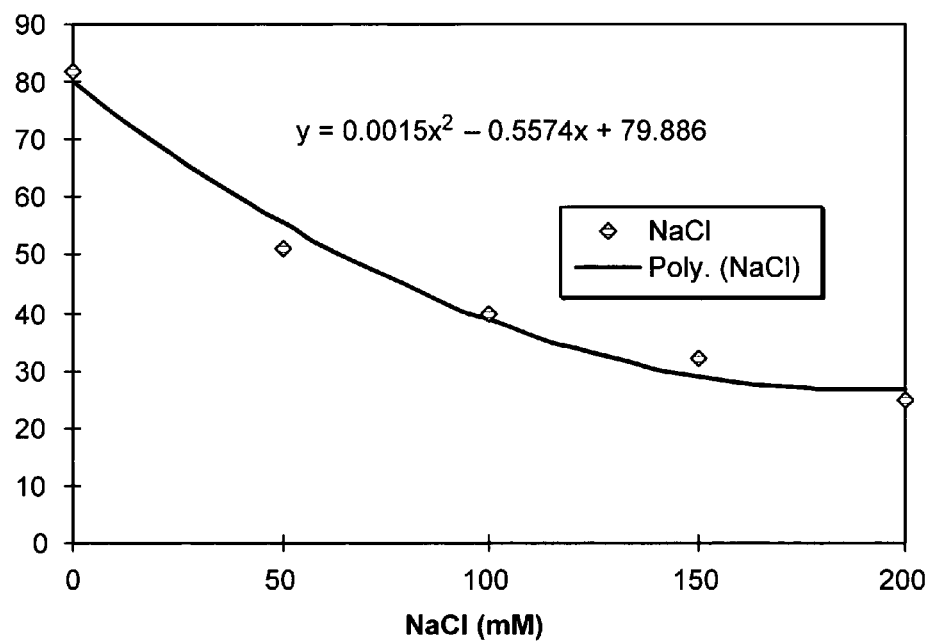
FIG. 7 is a graph that illustrates the NaCl dependency of α-crystallin in inhibiting elastase activity. One µg of elastase was incubated with 5 µl of α-crystallin conjugated sepharose in the presence of 0–200 mM NaCl. Increasing the NaCl concentration reduced the ability of α-crystallin to inhibit elastase activity.

In order to understand the salt dependance of inhibiting elastase by α-crystallin sepharose, the elastase activity assays were repeated in the presence of various concentrations of sodium chloride. FIG. 7 is a graph that illustrates the NaCl dependency of α-crystallin in inhibiting elastase activity. One μg of elastase was incubated with 5 μl of α-crystallin conjugated sepharose in the presence of 0–200 mM NaCl. Increasing the NaCl concentration reduced the ability of α-crystallin to inhibit elastase activity. It was determined that α-crystallin sepharose strongly inhibited elastase activity at low ionic strength (<50 mM). At higher ionic strength (200 mM) the % inhibition of elastase decreased to 30%. Findings indicate that the optimal conditions for the pre-column filter resin is neutral pH (7–8) and low ionic strength.

For gel filtration chromatography a pre-column filter was placed in series with the column during the entire run. After collecting the protease free fractions from the column run, the prepclean resin was taken offline and used for the next prep or if the performance of the PrepClean resin decreased, then it could be cleaned with 0.1M glycine (pH 2.5). The low pH removed the bound proteases, thereby regenerating the column.

For ion exchange chromatography it is envisioned that the column would be placed in series with the resolving column as above. In this case, after the protein is loaded and washed in low salt, the pre-column filter would be removed just prior to running the salt gradient. Finally after extended use the pre-column filter could be rejuvenated with low pH as described above.

Modifications and variations can be made to the disclosed embodiments without departing from the subject and spirit of the invention as defined in the following claims. Such modifications and variations, as included within the scope of these claims, are meant to be considered part of the invention as described.

What is claimed is:

1. A method for protecting a protein from proteolysis during Purification, comprising the step of contacting a sample that includes a protein with a resin material that is coupled to an alpha-crystallin protein selected from the group consisting of p26, SicA and alpha A crystallin protein, the contact occurring at a pH in the range of from about 7 to about 8.

2. The method of claim 1, wherein the contact occurs at a salt concentration of 50 mM or less.

3. The method of claim 1, wherein the alpha crystallin protein is a bovine alpha A crystallin protein.

4. The method of claim 1, wherein the alpha crystallin protein has an ability to inhibit proteases.

5. The method of claim 1, wherein the resin material includes at least one of the materials selected from the group consisting of agarose, a 6-aminohexanoic acid matrix material, and an epoxy-activated matrix material.

* * * * *